United States Patent [19]

Sullivan

[11] 4,094,119

[45] June 13, 1978

[54] METHOD OF MAKING A PRODUCT FOR DISPENSING A VOLATILE SUBSTANCE

[75] Inventor: William E. Sullivan, Columbia, S.C.

[73] Assignee: The Risdon Manufacturing Company, Naugatuck, Conn.

[21] Appl. No.: 778,855

[22] Filed: Mar. 18, 1977

[51] Int. Cl.² .................... B65B 29/00; A24F 25/00
[52] U.S. Cl. ........................................ 53/4; 53/28; 53/29; 53/37; 156/73.1; 156/290; 206/205; 239/56
[58] Field of Search ............... 53/4, 21 FC, 27, 28, 53/29, 36, 37, 39; 206/0.5, 205; 239/53, 55, 56; 156/73.1, 290

[56] References Cited

U.S. PATENT DOCUMENTS

| | | | |
|---|---|---|---|
| 3,415,702 | 12/1968 | Bauder | 53/4 X |
| 3,815,828 | 6/1974 | Engel | 239/56 |
| 3,942,634 | 3/1976 | Gandi et al. | 206/205 X |

Primary Examiner—Robert Louis Spruill
Attorney, Agent, or Firm—St. Onge, Mayers, Steward & Reens

[57] ABSTRACT

A method of making a product, which holds and dispenses a volatile substance, comprises the steps of advancing a backing material, a reservoir material and a third material, that is permeable to the volatile substance, from respective supplies into close proximity to each other with the reservoir material lying between the backing and permeable materials. The volatile substance is then supplied to the reservoir material to be absorbed thereby. The three materials are fused together in a pattern defining a closed loop periphery to seal the reservoir material between the backing and reservoir materials at the periphery and thereby form the product.

10 Claims, 5 Drawing Figures

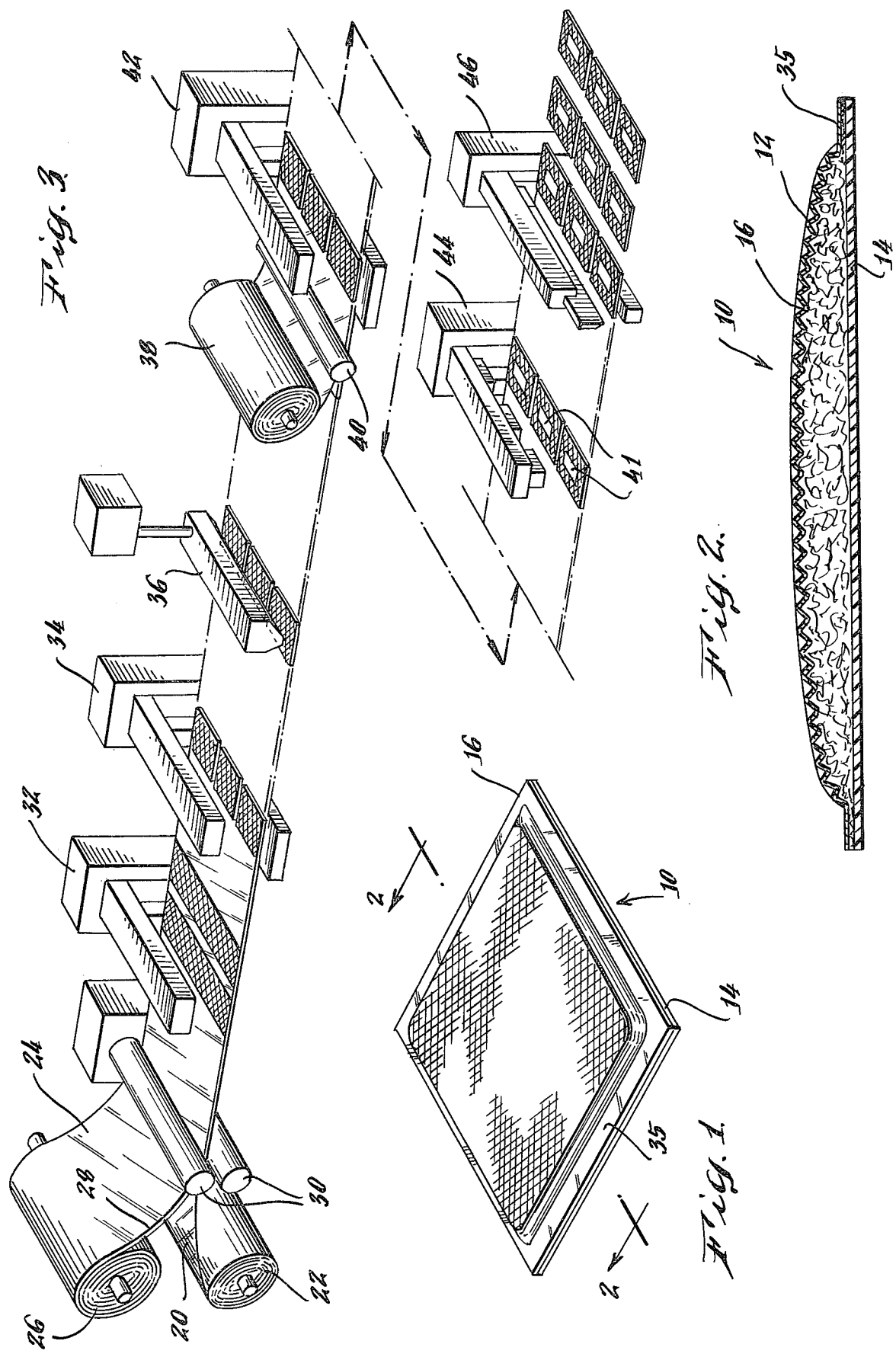

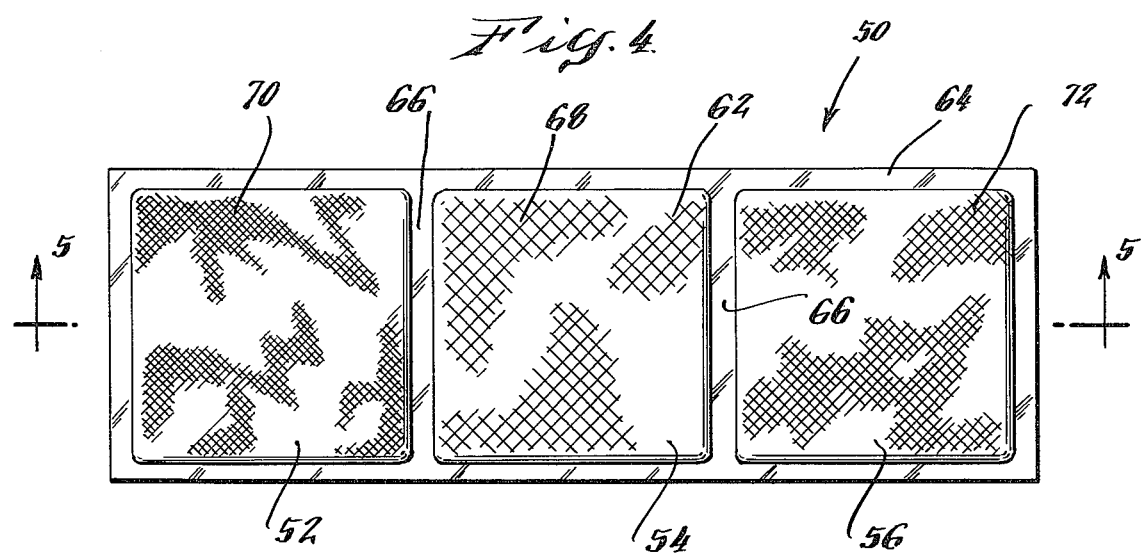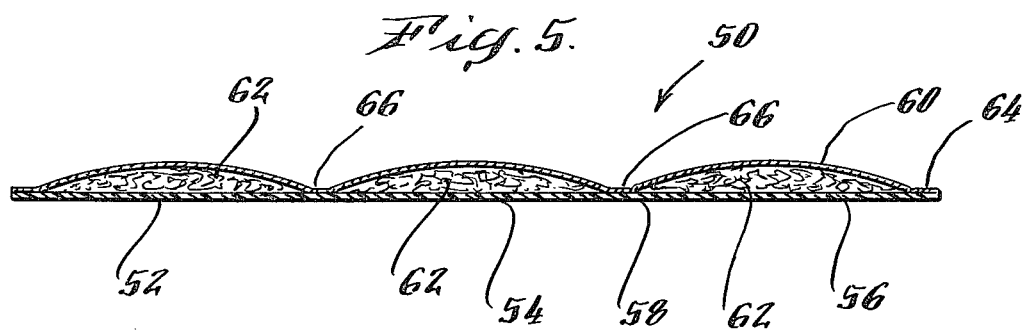

METHOD OF MAKING A PRODUCT FOR DISPENSING A VOLATILE SUBSTANCE

BACKGROUND OF THE INVENTION

1. Field of the Invention

The present invention relates to a product, and a method for making the product, that releases a volatile substance into the environment in a controlled manner. In particular, this invention relates to a method of making a product that contains the volatile substance for controlled release over an extended time while preventing it from spilling or oozing in liquid form.

Many consumer products such as room deodorizers, insecticides, germicides, fragrances and the like are volatile and may be released and dispersed in an area to be treated merely by being exposed therein. Devices for dispensing these products are also available in many forms such as liquid and wick systems, blotter systems and gel systems. However, the volatile substances may be subject to spillage, oozing or waste in each of these systems. Furthermore, methods of packaging such substances are subject to limitations imposed by the package itself. For example, liquids that are sold in bottles, cans or other rigid containers require relatively complex and expensive bottling or canning apparatus.

2. Description of the Prior Art

Various devices and methods for containing a volatile substance and for controlling the release of vapor from the substance are presently known. U.S. Patent application Ser. No. 731,300 (Sullivan & Meetze), assigned to the assignee of the present invention, discloses a device for releasing a volatile substance that includes a reservoir of substance-adsorbent material encapsulated in an envelope, at least a portion of which comprises a permeable material having porosity at least equal to ultramicroporosity. The permeable envelope portion has a greater affinity for the substance than does the reservoir material. The remainder of the envelope comprises a material impermeable to the substance. Accordingly, the substance permeates through the permeable envelope portion to be released in vapor form into the environment. The method of the present invention can be used to make devices of this type.

Other devices for releasing a volatile substance are disclosed in U.S. Pat. Nos. 3,216,882 (Feldt et al.); 3,770,199 (Hoek et al.) and in U.S. Pat. No. 4,035,451 (Tringali), assigned to the assignee of the present invention.

Methods and apparatus for making envelopes which are filled with various substances are also known. For example, U.S. Pat. Nos. 2,616,232 (Meyer); 2,970,414 (Rohdin); 3,007,848 (Stroop); 3,069,273 (Wayne); 3,495,992 (De For); and 3,978,636 (Clancy) disclose apparatus and methods for producing packages from two layers of endless film material from two supplies. The product that is held by the package may be added before or after final package formation and is completely encapsulated thereby. However, the methods of packaging a solid or gelatinous substance, such as those disclosed in the Stroop and Clancy Patents, separate the substance into discreet quantities so that the enveloping materials may be sealed without interference therefrom. Accordingly, the substance should be accurately positioned between the enveloping materials to prevent poor sealing.

U.S. Pat. No. 3,391,047 (Kopp) discloses an apparatus for manufacturing a dual compartment sachet. Three layers of a thin film are welded together to form the two compartments which may be filled with different materials.

U.S. Pat. No. 3,070,225 (Schwartz) discloses a package for a bandage and a method of making the package.

None of the patents noted above disclose a method for making a product which holds and dispenses a volatile product, nor do any disclose a method of making a package comprised of a backing material, a reservoir material and a permeable material that automatically seals the reservoir material about a closed periphery. Moreover, no disclosure is made of a process for making a device, that dispenses a volatile product in a manner that controls the rate at which the product is volatilized.

SUMMARY OF THE INVENTION

In its preferred embodiment, to be described below in detail, the method of the present invention is used to produce a device of the type disclosed in U.S. Patent application Ser. No. 731,300 (Sullivan & Meetze), that holds and dispenses a volatile substance such as a liquid fragrance, deodorant, germicide or insecticide. The method may include steps for forming the device to control the rate at which the substance volatilizes.

In the preferred embodiment, the method of the invention comprises the steps of continuously advancing a backing material from a supply and simultaneously continuously advancing an absorbent reservoir material into close proximity with the backing material. A third material, which is permeable to the volatile substance, is then advanced into close proximity to the reservoir material to form a multilayer strip with the reservoir material lying between the backing and permeable materials. The volatile substance is supplied to and absorbed by the reservoir material to be held thereby. To complete the package, the backing, reservoir and permeable materials are fused together in a pattern which defines a closed periphery in order to seal the reservoir material between the backing and permeable materials. That is, the fusing step compresses and seals the reservoir material at the closed periphery to prevent transfer of the volatile substance through the fused areas.

Because all three materials are advanced simultaneously to suitable apparatus for fusing them together in accordance with the method of the invention, problems of positioning the reservoir material to be properly enclosed by the enveloping materials are eliminated. The method of the present invention, rather than requiring that discreet amounts of the reservoir material be accurately positioned so that it does not lie between the enveloping materials, directly fuses the enclosed and enclosing materials together. Moreover, the fusing step automatically seals the absorbent reservoir material at a closed periphery to prevent spillage or oozing of the volatile substance therefrom.

The method may also include steps for fusing the surface of the permeable material in a preselected pattern that permits a given area of unfused material to remain. By doing this, the area through which the volatile substance may permeate for release into the environment may be precisely controlled. As will be explained in greater detail below, the size of this area is related to the rate at which the volatile substance is released and, hence, to the effective life of the device.

Accordingly, it is an object of the present invention to provide a method for producing devices that release the volatile substance into the environment in a controlled manner. This method avoids steps required by certain prior art methods and accordingly is more simple and more economical than those methods.

Other objects, aspects, and advantages of the present invention will be pointed out and will be understood from the following detailed description provided below in conjunction with the accompanying drawings.

BRIEF DESCRIPTION OF THE DRAWINGS

FIG. 1 is a perspective view of one form of the device for releasing a volatile product into the environment in a controlled manner which may be made in accordance with the method of the present invention.

FIG. 2 is a vertical cross-sectional view of the device taken through plane 2—2 in FIG. 1.

FIG. 3 is a diagrammatic representation of apparatus for performing the steps of the method of the present invention.

FIG. 4 is a top plan view of a second form of the device, which may be made in accordance with the method of the present invention, that illustrates several fused patterns of a multicompartment device for regulating the rates at which several volatile substances are released.

FIG. 5 is a vertical cross-sectional view taken through plane 5—5 in FIG. 4.

DETAILED DESCRIPTION OF THE PREFERRED EMBODIMENT

Prior to explaining the method of the present invention it is helpful to describe the device which the method is designed to produce. As shown in FIGS. 1 and 2, this device, generally indicated at 10, for releasing a volatile substance into the environment in a controlled manner, comprises a reservoir 12 which may be in the form of a relatively thick pad of substance-absorbent material. In its preferred form, this reservoir material is highly fibrous, non-woven polypropylene. However, it may be made of any other material which is fusable or weldable in a manner to be described below in detail. It should, however, be absorbent of the volatile substance such as, for example, be a fragrance, an insecticide, a germicide, or the like which the device is intended to hold and dispense.

The device further comprises a relatively thick backing layer 14 that may, for example, also be polypropylene. This backing material serves to give the device form and rigidity if desired. However, the backing layer need not be rigid but rather be pliable or may be permeable as is another layer of the device so that the device will conform to a specially shaped cavity or other mounting arrangement. In either case, this backing layer should be made of a material which is fusable or weldable in a manner described below.

Mounted above the reservoir material 12 on the side of the device opposite the backing layer 14 is a layer of microporous or ultramicroporous material 16 that is permeable to the volatile substance. For example, this porous material may be gelled cellulose triacetate which is available from Moleculon Research Corporation, Cambridge, Mass., and is constructed in in accordance with U.S. Pat. No. 3,846,404 (Nichols). Alternatively, the microporous material may be a microporous polypropylene sold under the name "CELGARD" by the Celanese Corporation. In either case, the microporous material should be fusable with the reservoir and backing materials as will be described.

It can be readily appreciated from the drawings that the volume of the reservoir is substantially greater than the volume of the ultramicroporous sheet material. Accordingly, the reservoir is capable of storing an amount of volatile substance much greater than that which might be impregnated in the ultramicorporous sheet.

Further, it has been found that when a device is constructed in the fashion to be described below, with the materials specified, a preferential migration of the volatile substance takes place through the permeable material from the reservoir. Moreover, when the permeable material is gelled cellulose triacetate, migration of the substance occurs in its non-vapor, that is, liquid form. Vaporization of the liquid then takes place on the exterior surface of the ultramicroporous material for subsequent diffusion into the area to be treated. It is believed that the ultramicroporous material has a greater affinity for the volatile substance than does the larger porous reservoir. Moreover, it has been found that the preferential migration described above essentially exhausts all of the substance originally stored in the reservoir so that little or none is wasted when the device is discarded.

The device also provides a more uniform continuous release of the volatile substance than a device composed of ultramicroporous material alone. For example, pores in gelled cellulous triacetate tend to collapse as a volatile substance is exhausted from them. Therefore, the release rate slows as more of the substance is used up. However, in the device of the invention, the substance tends to migrate through the ultramicroporous sheet at a uniform rate. That is, the amount of substance in the sheet at any one time is substantially constant until the reservoir is nearly exhausted. Thus, a continuous uniform substance release rate may be maintained for an extended period of time while the relatively large amount of substance initially present in the reservoir is volatilized.

While a preferential migration of volatile substance through the permeable material occurs when gelled cellulous triacetate is used, microporous polypropylene, such as "CELGARD" acts as a liquid barrier, being permeable to vapor which volatilizes from the substance. Accordingly, vaporization takes place within the reservoir and the vapor is ultimately permeated through the permeable material.

In addition, ultramicroporous or microporous polyethylene film may be used as the permeable material. Polyethylene is particularly well suited for dispensing highly volatile substances since it permits volatilization only at a slow rate.

The device described in detail above may be made by the method of the present invention which will now be described with reference to the apparatus diagrammatically illustrated in FIG. 3.

This apparatus is arranged to produce a three compartment device which will be described further below. In accordance with this method, an endless sheet 20 of a relatively thick layer of backing material such as polypropylene 14 is fed or continuously advanced from a supply roll 22. Simultaneously, an endless sheet 24 of a relatively thin layer of microporous polypropylene 16, preferably "CELGARD", is fed or continuously advanced from a supply roll 26. For purposes of illustration, the microporous polypropylene supply roll 26 is mounted above the backing layer supply roll 22. However, of course, this arrangement may be reversed.

In accordance with the preferred embodiment of the method of the present invention, a thick layer 28 of nonwoven polypropylene, which serves as the volatile substance reservoir 12, is loosely bonded to the microporous polypropylene layer 24 prior to being wound onto roll 26. In this way, as the microporous layer is advanced, the reservoir material layer is simultaneously advanced. Alternatively, the reservoir material may be loosely bonded to the backing layer 20. In either case, by feeding an endless supply of the backing or microporus layers together with the reservoir layer, problems associated with prior art methods of positioning the contents of an envelope properly therein are eliminated. No complex apparatus for delivering the reservoir or other encapsulated material to precise locations relative to the envelope materials need be used.

The three respective materials are fed through the nip of opposed feed rollers 30 to a first fusing station 32. As shown in FIG. 3, this station is mounted to fuse a predetermined pattern on the surface of the microporous layer 24 which leaves all but a preselected area of the permeable material nonporous. In this manner, this preselected area of the permeable material is left permeable to the volatile substance. The size of the permeable area determines the rate at which the substance permeates therethrough and accordingly determines the rate at which the substance volatilzes from the device. This aspect of the invention will be described in greater detail below.

From the pattern fusing station 32, the assembled materials are fed to a main fusing station 34 that may, for example, be an ultrasonic welder. Here all three materials, namely the microporous, backing, and reservoir materials are fused together in a pattern that defines at least one closed loop periphery 35 (FIGS. 1 and 2). (The three compartment device has three such closed loop peripheries). At this periphery 35, the reservoir material is compressed, as best seen in FIG. 2, to a degree that renders it nonporous and nonpermeable to the volatile substance. Accordingly, a boundary preventing transfer of the volatile substance through all but the permeable material is formed. Moreover, as described above, this sealed periphery is made without reference to the precise positioning of the reservoir material since the reservoir material is actually compressed sealed between the microporous and backing materials when fused by the ultrasonic welder.

After the reservoir and permeable backing materials are fused together, the continuously advancing assembled sheets are fed to a volatile substance filling head 36 which meters volatile substance through the permeable material into the non-woven polypropylene reservoir material in precise amounts.

For storage, the device may be provided with a protective sealing layer fed from a supply roll 38 into close proximity with the permeable layer. This layer is fed by a feed roller 40 under a sonic welding station 42 where it is bonded to the closed top of periphery 35 to prevent volatilization of the substance prior to the time desired. The sealing layer may be, for example, a metalized "Mylar", available from E. I. DuPont de Nemours, Inc. or any other nonporous material which is impermeable to the volatile substance. The sonic welder is arranged to attach the sealing layer to the remainder of the device so that it may be easily removed prior to use.

The method of the present invention may also include the step of attaching a label or imprinting the sealable layer with any logo 41 desired at an imprinting station 44. The continuously advancing fused materials are then fed to a severing station 46 which separates the individual devices formed from the continuously advancing material which have been fused at spaced locations. Finally, the individual devices may be packed for shipment or sale.

It can be readily appreciated that the method of the present invention economically and accurately forms the device described above. There is no need for precise positioning of the reservoir material as is frequently done with comparable material in prior art methods for making solid or gelatinous products enclosed by an envelope. Moreover, the device of the present invention is formed so that no leakage or oozing of the volatile substance may occur through the sealed closed loop periphery since the reservoir material is compressed and fused together thereat.

The apparatus and method of the present invention may also be used to form a multicompartment device such as the second embodiment shown in U.S. Patent application Ser. No. 731,300 (Sullivan & Meetze). This device is adapted to dispense a volatile substance having more than one volatile chemical constituent that may be separated by, for example, distillation or may be purchased separately. The second device, shown in FIGS. 4 and 5 and generally indicated at 50, has, for example, three separate compartments 52, 54, and 56, one for each of three constituents. The three compartments of the device are simultaneously made in accordance with the method described above. All comprise a single backing layer 58 of, for example, a non-porous polypropylene and a single permeable upper layer 60. A reservoir material 62 of non-woven polypropylene is fused between the upper and lower layers into the three separate compartments defined by an outside closed loop periphery 64 and sealed dividing barriers 66.

Further, at the fusing station 32 the fusing head is arranged to fuse the microporous layer of each compartment into a pattern which leaves a precise area of microporous material unfused. This area is determined by the rate at which the substance contained in the respective compartments volatilizes. That is, the total area of permeable substance remaining is inversely proportional to the rate of volatilization of the constituent of the substance to be filled in the respective compartment. Thus, for example, the compartment 54 in the center of the device has a large open area of microporous material indicated by cross hatching 68, which results from a relatively course fused pattern, that enhances the volatilization of a substance constituent which ordinarily has a slow rate of vaporization. Conversely, the left compartment 52 has a smaller open area indicated by cross hatching 70, which results from a less coursely fused pattern, that slows release of a constituent having a normally rapid rate of vaporization. The right compartment 56 has an intermediate amount of open area remaining unfused indicated by cross hatching 72 for a constituent having an intermediate of vaporization.

By calculating the respective rates of vaporization of the respective components and adapting the area of open permeable material which remains after the pattern fusing step, each constituent and hence, the entire substance may be volatilized at a substantially uniform rate to maintain a substantially uniform fragrance, germicidal effect, and insecticidal effect, or the like depending on the substance filling device.

As can be seen from the above description, the method of making this device is substantially the same as that described with reference to the first form thereof. However, the fusing head is modified to fuse the microporous cover of each of the respective compartments in a pattern determined by the rate of vaporization of the substance constituent supplied to its respective reservoir.

It will be appreciated that while ultrasonic welding is described as the material fusing process, other techniques may be used. For example, heat sealing or "sonic sewing" techniques can be used.

Accordingly, although a specific embodiment of the method of the present invention has been described above in detail, it is to be understood that this is for purposes of illustration. Modifications may be made to the steps of this method in order to adapt it to particular applications.

I claim:

1. A method of producing a product for holding and dispensing a volatile substance in vapor form into the environment, said method comprising the steps of:
    A. providing a backing material;
    B. placing a reservoir material, capable of holding the volatile substance, in close proximity to the backing material;
    C. placing a material permeable to the volatile substance in close proximity to the reservoir material;
    D. supplying the volatile substance to the reservoir material to be held thereby; and
    E. fusing the backing, reservoir and permeable materials together in a pattern defining a closed loop periphery to seal the reservoir material between the backing and permeable materials, said fusing step compressing and sealing the reservoir material to prevent transfer of the substance through the fused periphery.

2. The method of producing a product for holding and dispensing a volatile substance in vapor form as claimed in claim 1 further comprising the steps of:
    F. placing a material, impermeable to the volatile substance, in close proximity to the permeable substance, and
    G. removably sealing said impermeable material to said permeable material at the closed loop periphery to prevent volatilization of the substance until the impermeable material is removed from the product.

3. The method of producing a product for holding and dispensing a volatile substance in vapor form as claimed in claim 1 wherein said backing materials are also permeable to the volatile substance.

4. A method of producing a product for holding and dispensing a volatile substance in vapor form into the environment, said method comprising the steps of:
    A. feeding an elongated backing material from a supply;
    B. feeding an elongated reservoir material, capable of holding the volatile substance, from a supply into close proximity to the backing material;
    C. feeding an elongated material, permeable to the volatile substance, from a supply into close proximity to the reservoir material;
    D. supplying the volatile substance to the reservoir material to be held thereby; and
    E. fusing the backing, reservoir, and permeable materials together in a pattern defining a closed loop periphery to seal the reservoir material between the backing and permeable materials and thereby form the product.

5. The method of producing a product for holding and dispensing a volatile substance in vapor form as claimed in claim 4 wherein each of said feeding steps comprises:
    advancing the respective material from a supply roll thereof.

6. The method of producing a product for holding and dispensing a volatile substance in vapor form as claimed in claim 5 wherein said fusing step is performed at spaced locations as the assembled materials are advanced and wherein said method further comprises the step of:
    F. separating the advancing materials at the fused locations to form individual products.

7. The method of producing a product for holding and dispensing a volatile substance in vapor form as claimed in claim 4 wherein the fusing step comprises:
    ultrasonically welding the materials together.

8. The method of producing a product for holding and dispensing a volatile substance in vapor form as claimed in claim 4 further comprising the steps of:
    F. placing a material, impermeable to the volatile substance in close proximity to the permeable substance; and
    G. removably sealing the impermeable material to the permeable material at the closed loop periphery to prevent volatilization of the substance until the impermeable material is removed from the product.

9. The method of producing a product for holding and dispensing a volatile substance in vapor form as claimed in claim 4 further comprising the step of:
    F. fusing all but a preselected area of the permeable material to render all but said area impermeable to the volatile substances, the size of the remaining permeable area determining the rate of which the substance permeates therethrough and is volatilized from the product.

10. The method of producing a product for holding and dispensing a volatile substance in vapor form as claimed in claim 4 further comprising the step of:
    F. bonding one of the backing and permeable materials and the reservoir material together prior to said feeding steps whereby feeding of the reservoir material and the material bonded thereto occurs simultaneously.

* * * * *